US009345610B2

(12) United States Patent
Modglin

(10) Patent No.: US 9,345,610 B2
(45) Date of Patent: May 24, 2016

(54) DORSAL LUMBAR EXTENSION BRACE WITH TENSIONING SYSTEM

(71) Applicant: DeRoyal Industries, Inc., Powell, TN (US)

(72) Inventor: Michael D. Modglin, Braselton, GA (US)

(73) Assignee: DeRoyal Industries, Inc., Powell, TN (US)

(*) Notice: Subject to any disclaimer, the term of this patent is extended or adjusted under 35 U.S.C. 154(b) by 101 days.

(21) Appl. No.: 14/169,600

(22) Filed: Jan. 31, 2014

(65) Prior Publication Data

US 2014/0221893 A1 Aug. 7, 2014

Related U.S. Application Data

(60) Provisional application No. 61/761,946, filed on Feb. 7, 2013.

(51) Int. Cl.
*A61F 5/00* (2006.01)
*A61F 5/02* (2006.01)

(52) U.S. Cl.
CPC ............ *A61F 5/028* (2013.01); *A61F 5/026* (2013.01)

(58) Field of Classification Search
CPC ......... A61F 5/024; A61F 5/026; A61F 5/028; A61F 5/04; A61F 5/055; A61F 5/03; A61F 5/022; A61F 2005/0179; A61F 5/01; A61F 5/0102; A61F 5/042; A61F 5/048; A61F 5/0125; A61F 2005/0134; A61F 2005/016; A61F 2005/0167; A61H 1/008; A45F 3/08; A45F 3/04; A45F 2003/045; A45F 2003/125; A45F 2003/144; A45F 3/06; A61B 6/107; A61B 6/4423; G21F 3/02; A45C 3/001; A45C 7/00
USPC ..................................... 602/19; 128/874–875
See application file for complete search history.

(56) References Cited

U.S. PATENT DOCUMENTS

| 1,371,690 | A | * | 3/1921 | Kelly .................................. 2/44 |
| 1,678,584 | A | * | 7/1928 | Branson ............................. 2/44 |
| 5,951,591 | A | * | 9/1999 | Roberts ......................... 606/241 |
| 7,789,844 | B1 | | 9/2010 | Allen |
| 8,066,654 | B2 | | 11/2011 | Sandifer et al. |
| 8,308,670 | B2 | | 11/2012 | Sandifer et al. |
| 8,556,840 | B2 | * | 10/2013 | Burke et al. .................... 602/19 |
| 2011/0152737 | A1 | | 6/2011 | Burke et al. |
| 2013/0184652 | A1 | | 7/2013 | Ingimundarson et al. |

FOREIGN PATENT DOCUMENTS

WO 2011150401 A1 12/2011
WO 2013156394 A1 10/2013

OTHER PUBLICATIONS

International Search Report and Written Opinion, PCT/US2014/014135, date of mailing Apr. 9, 2014—13 pages.

* cited by examiner

*Primary Examiner* — Michael Brown
(74) *Attorney, Agent, or Firm* — Luedeka Neely Group, PC

(57) ABSTRACT

A spinal brace having a waist or abdominal portion, a dorsal lumbar insert, shoulder straps, and one or more cable tensioning systems that enables a user to tighten the waist or abdominal portion while at the same time tightening the shoulder straps to encourage extension.

8 Claims, 7 Drawing Sheets

DORSAL LUMBAR EXTENSION BRACE WITH TENSIONING SYSTEM

CROSS-REFERENCE TO RELATED APPLICATION

This application claims priority to U.S. Provisional Application Ser. No. 61/761,946 filed Feb. 7, 2013, entitled Dorsal Lumbar Extension Brace With Tensioning System, incorporated by reference herein in its entirety.

FIELD

This disclosure relates to the field of orthopedic bracing. More particularly, this disclosure relates to dorsal lumbar extension braces incorporating cable reels or other tensioning systems that enable selective tensioning of the waist or abdominal portion of the brace while at the same time tensioning the shoulder straps to encourage extension in/of the brace.

BACKGROUND

Improvement is desired in the provision of braces. In particular, what is desired is improvement in the tensioning of braces of the type having a waist belt and shoulder straps.

The disclosure advantageously provides a spinal orthosis or brace having a waist or abdominal portion, a dorsal lumbar extension, shoulder straps, and one or more cable tensioning systems that enables a user to tighten the waist or abdominal portion while at the same time tightening the shoulder straps.

Braces according to the disclosure advantageously enable a modular bracing system that fits a wide range of patient sizes to cut down on inventory needs, while at the same time is adjustable to enable the brace to be configured to fit a wide variety of patient indications.

SUMMARY

The disclosure relates to spinal braces having a waist or abdominal portion, and one or more shoulder straps, with a cable that permits simultaneous adjustment of the waist portion and the shoulder strap.

In one aspect, the spinal brace includes a waist portion configured for encircling and being adjustably tensionable about the waist of a user; a dorsal lumbar extension extending from a rear portion of the waist portion; a shoulder strap positionable to extend over a shoulder of the user and connectable to both the waist portion and the dorsal lumbar extension; a cable connectable to both the waist portion and the shoulder strap for tensioning the waist portion and the shoulder strap; and a cable tensioner operably associated with the cable to adjust the tension the cable. Adjustment of the tension of the cable simultaneously adjusts the tension of the waist portion of the brace about the waist of the user and the tension of the shoulder strap.

In another aspect, the spinal brace includes a waist portion configured for encircling and being adjustably tensionable about the waist of a user; a shoulder strap positionable to extend over a shoulder of the user and connectable to the waist portion; a cable connectable to both the waist portion and the shoulder strap for tensioning the waist portion and the shoulder strap; and a cable tensioner operably associated with the cable to adjust the tension the cable. Adjustment of the tension of the cable simultaneously adjusts the tension of the waist portion of the brace about the waist of the user and the tension of the shoulder strap.

In yet a further aspect, the spinal brace includes a waist portion configured for encircling and being adjustably tensionable about the waist of a user, the waist portion including a posterior portion, an anterior portion, and first and second side members, each made of a conformable and flexible material. The first and second side members are each releasably and adjustably connectable to the posterior member and the anterior member to enable the formation of the waist portion in a configuration that will snugly encircle the waist of a user.

The spinal brace also includes a dorsal lumbar extension extending from the posterior portion of the waist portion. A first shoulder strap is positionable to extend over a first shoulder of the user and is connectable to both the first waist portion and the dorsal lumbar extension; and a second shoulder strap is positionable to extend over a second shoulder of the user and is connectable to both the second waist portion and the dorsal lumbar extension.

A first cable is connectable to both the first waist portion and the first shoulder strap for tensioning the first waist portion and the first shoulder strap; and a second cable is connectable to both the second waist portion and the second shoulder strap for tensioning the second waist portion and the second shoulder strap.

The spinal brace includes a first cable tensioner operably associated with the first cable to adjust the tension the first cable, and a second cable tensioner operably associated with the second cable to adjust the tension the second cable. Adjustment of the tension of the first cable simultaneously adjusts the tension of the first waist portion of the brace and the tension of the first shoulder strap, and adjustment of the tension of the second cable simultaneously adjusts the tension of the second waist portion of the brace and the tension of the second shoulder strap.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
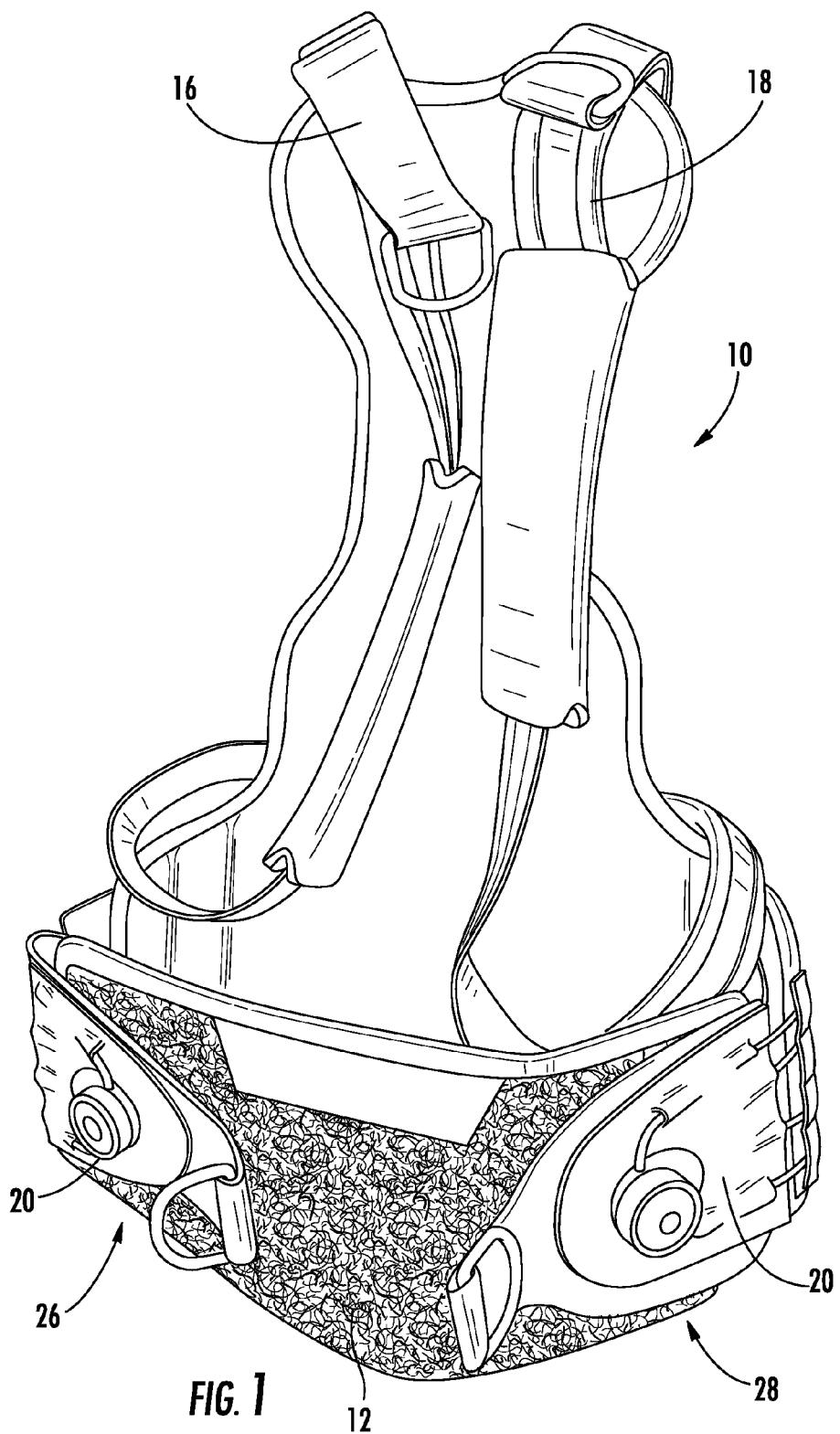
FIG. 1 is a front perspective view of a brace according to the disclosure.
Figure 2:
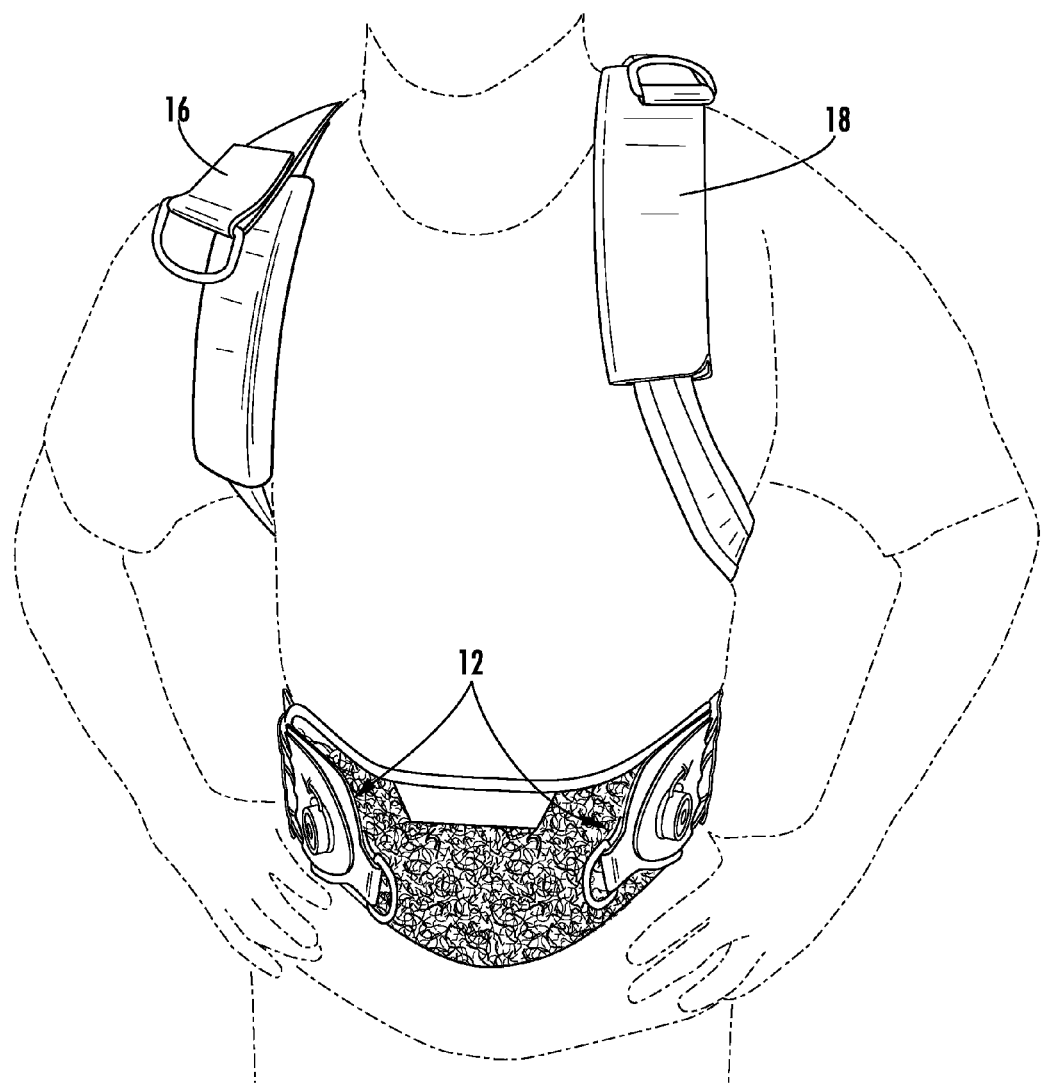
FIG. 2 is a front view of the brace of FIG. 1 installed on a user.
Figure 3:
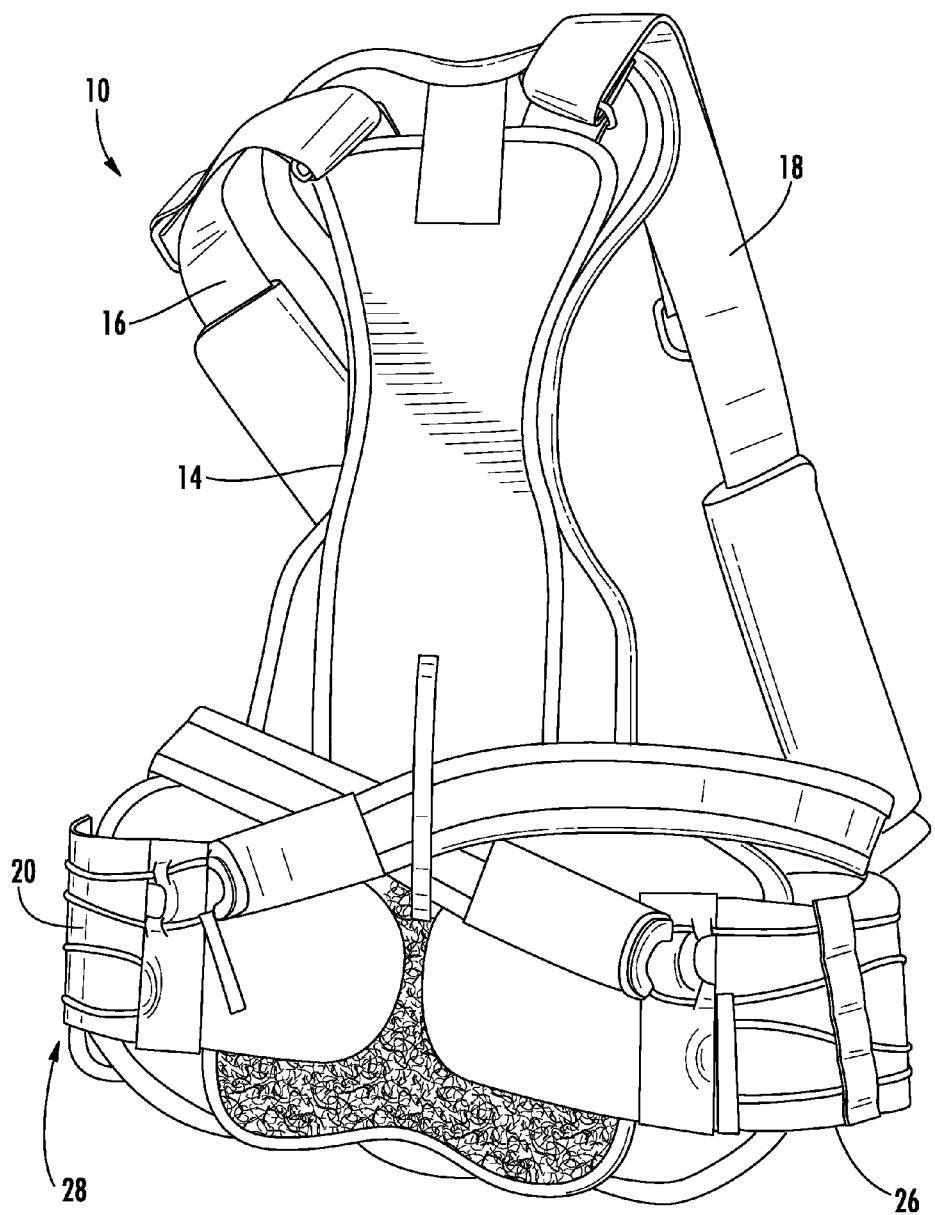
FIG. 3 is a rear perspective view of the brace of FIG. 1.
Figure 4:
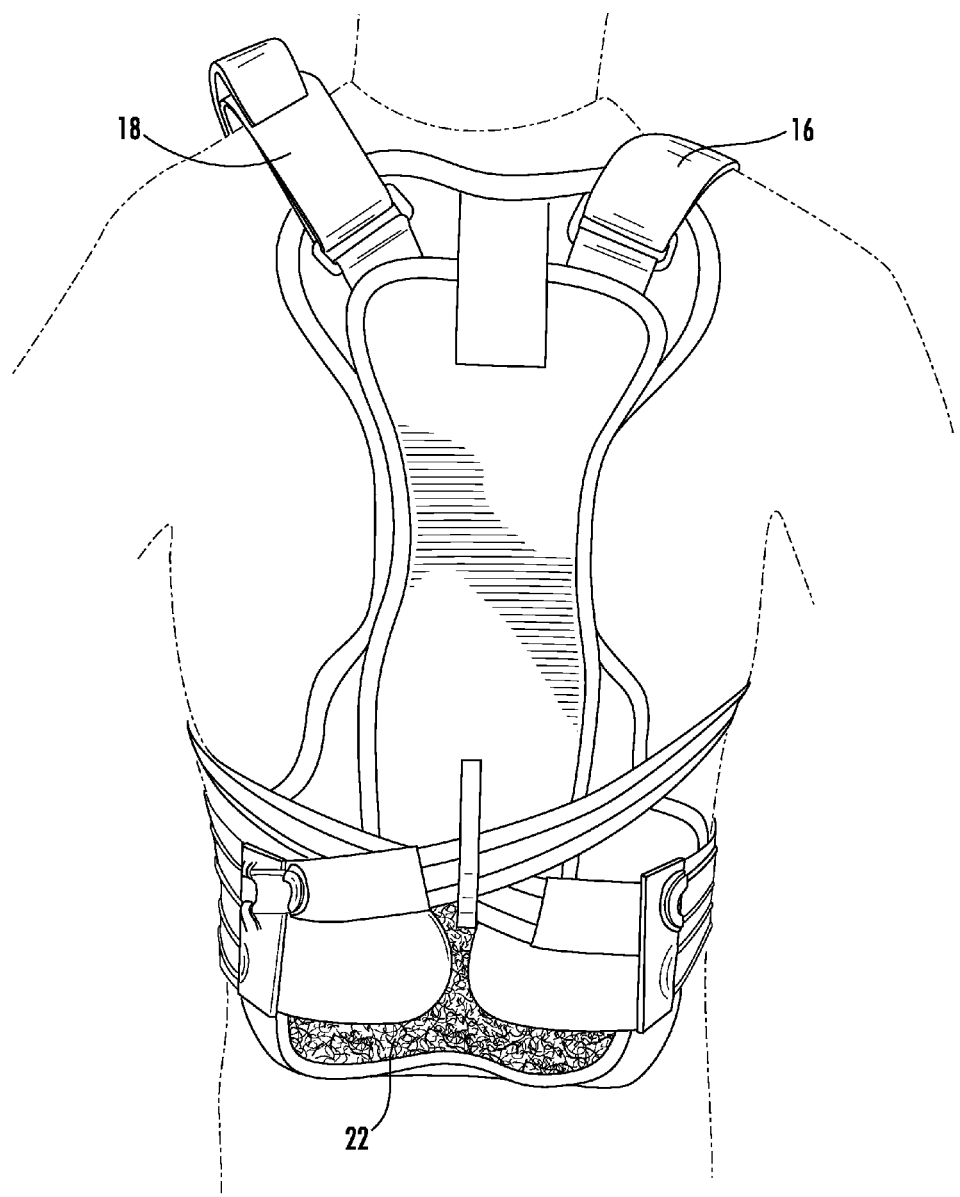
FIG. 4 a rear view of the brace of FIG. 1 installed on a user.
Figure 5:
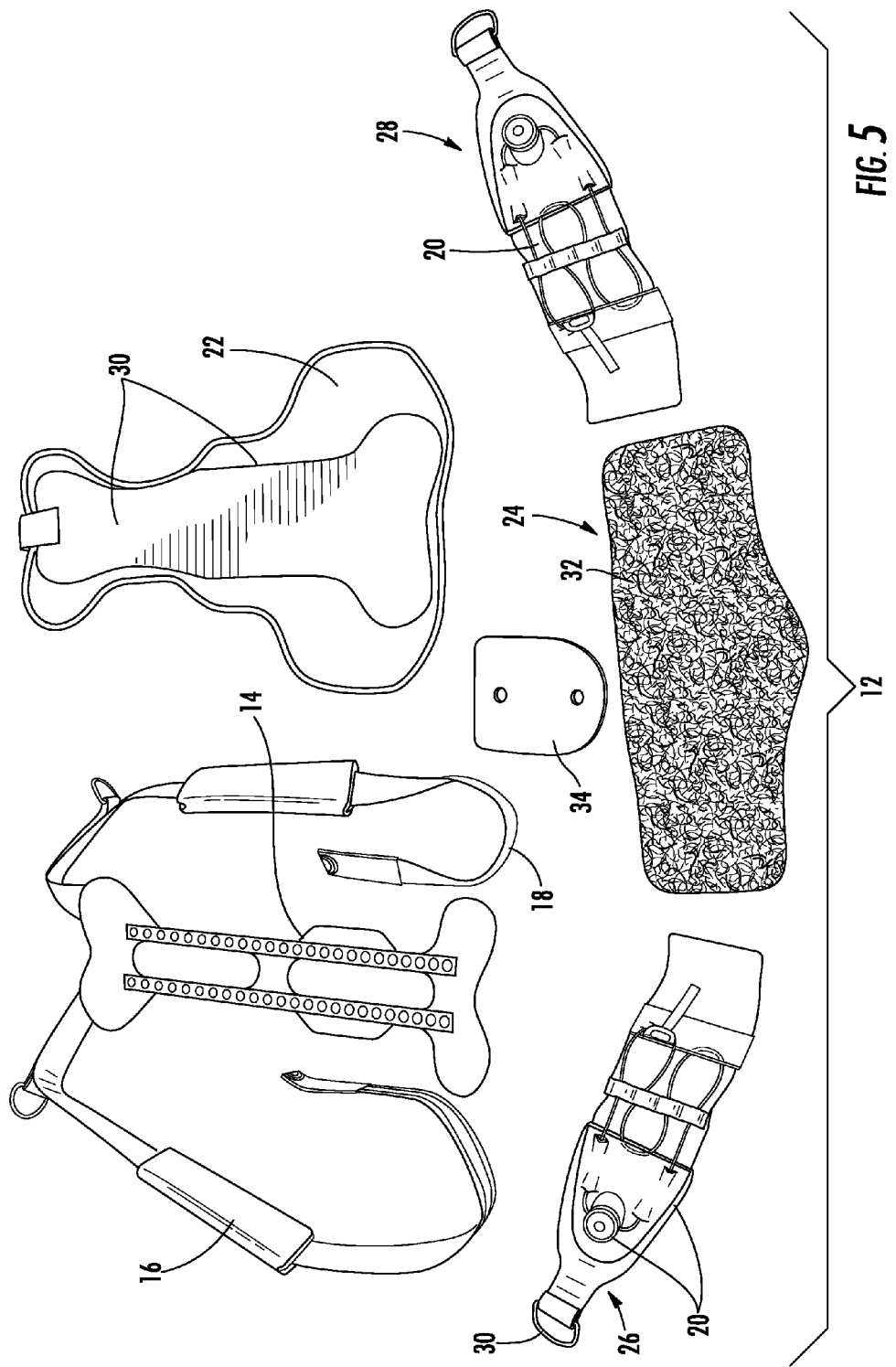
FIG. 5 is an exploded view of the brace of FIG. 1.

The disclosure relates to a spinal orthosis 10 having a waist or abdominal portion 12, a dorsal lumbar insert 14, shoulder straps 16 and 18 to promote extension, and one or more cable tensioning systems 20. The tensioning systems 20 enable a user to tighten or loosen the waist or abdominal portion 12 while at the same time tightening or loosening the shoulder straps 16 and 18 to promote a desired adjustment of the extension.

The waist portion 12 may include a posterior portion 22, an anterior portion 24, and side members 26 and 28, each made of a conformable and flexible material. The side members 26 and 28 each releasably and adjustably connect to the posterior member 22 and the anterior member 24 as by mating hook and loop material to enable the formation of the waist portion 12 in a configuration that will snugly encircle the waist of a user. A D-ring 30 is desirably located at the anterior end of each of the side members 26 and 28 for tensioning the side members 26 and 28. In this regard, the exterior surfaces of the posterior portion 22 and the anterior portion 24 may be made of a soft loop material and the side members 26 and 28 may have hook material at each end to releasably engage the loop material. As used herein, the terms waist and abdominal are interchangeable. The modular configuration of the described waist portion 12 advantageously fits a wide range of patient sizes to cut down on inventory needs.

The posterior portion 22 includes a vertically extending pocket 30 for receiving the dorsal lumbar insert 14. The anterior portion 24 includes a pocket 32 for receiving a rigid stay 34. The side members 26 and 28 are made of a lightweight and flexible elastic fabric, with each having one of the cable tensioning systems 20 located thereon as described more fully below.

The dorsal lumbar insert 14 is preferably a rigid or semi-rigid but adjustable extension. A particularly preferred rigid but adjustable extension is an extension available under the trade name NOBLE HINGE from DeRoyal Industries, Inc. of Powell, Tenn.

The shoulder strap 16 is an elongate flexible strap having one end adjustably connected to the dorsal lumbar insert 14 and the other end connectable to the cable tensioning system 20. For example, the end connected to the insert 14 may have a hook material applied thereto with the exterior of the strap 16 having a loop surface. The strap 16 may be passed through a D-ring or other connector on the insert 14 and overlapped to adjustably connect the strap 16 to the insert. The opposite end of the strap 16 includes a strap cable guide 40 for receiving a portion of a cable 42 of one of the cable tensioning systems 20. The guide 40 is configured so as to enable the cable 42 to be releasably engaged therewith, and may be provided as a hard plastic material having a groove into which the cable 42 may be seated. The shoulder strap 18 is substantially identical to the shoulder strap 16 and cooperates with the lumbar insert 14 and the other of the cable tensioning systems 20 in the same manner. It will be understood that while two separate straps are described, the straps may be provided as by a single length of material that serves to provide two straps that adjustably position about the shoulders in the manner of the straps 16 and 18.

In addition to the cable 42, the cable tensioning system 20 includes cable tensioning structure that functions to adjust the tension of the cable 42, such as a cable take-up 44, a plurality of fixed cable guides 46, and a releasable cable guide 48. The cable take-up 44 may be provided as by a cable reel or other structure that enables tension to be applied or removed from the cable 42. Suitable cable reel devices are available under the name BOA from Boa Technology, Inc. of Denver, Colo., and described in U.S. Pat. Nos. 7,954,204 and 7,992,261, incorporated by reference in their entireties. The fixed guides 46 may be provided as by strips of material sewn to the side members 26 and 28. The releasable cable guide 40 may be provided in the manner of the strap cable guide 40, and provided by a hard plastic material secured to one of the side members 26 and 28 and having a groove into which the cable 42 may be seated.

It will be appreciated that the brace 10 is configured with two of the tensioning systems 20. However, it will be understood that the brace 10 may be constructed to utilize a single cable tensioning system. Further, it will be understood that devices and structures other than cable reels may be used for adjusting cable tension. For example, the cables may be tensioned around fixed posts, be tensioned as by connection to a length of hook material that may be adjustably positioned to loop material of the brace, or by other structures that serve to enable adjustment of the tension and fixing of the tension of the cable as desired so that the tension supplied to the user by both the waist portion 12 and the straps 16/18 are simultaneously adjusted.

The brace 10 is installed by installing the waist portion 12 onto the waist of the user. For example, the anterior portion 24 is secured to one of the side members 26 or 28, and the posterior portion 22 is secured to one both the side members 26 and 28. The waist portion 12 is slipped around the waist of the user and the free one of the side members 26 or 28 is secured to the anterior portion 24. The D-rings 30 of each of the side members 26 and 28 may then be grasped, and the side members 26 and 28 re-positioned to snugly secure the brace 10 around the waist of the user. A single length of material may be used to provide the waist portion 12, with one or both of the tensioning systems 20 being utilized to adjust the tension thereof. However, to avoid initial adjustment of the tension and to avoid undue bunching and the like, the described structures are preferred.

Figure 6:
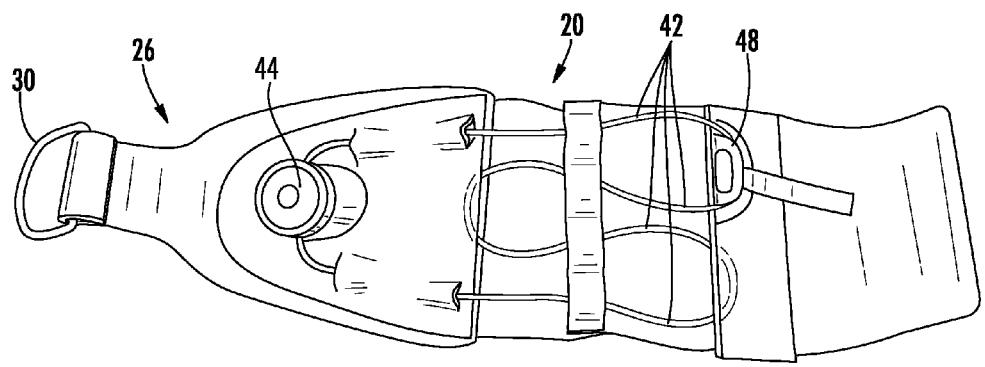
FIG. 6 shows a side member and a cable tensioning system of the brace of FIG. 1.
Figure 7:
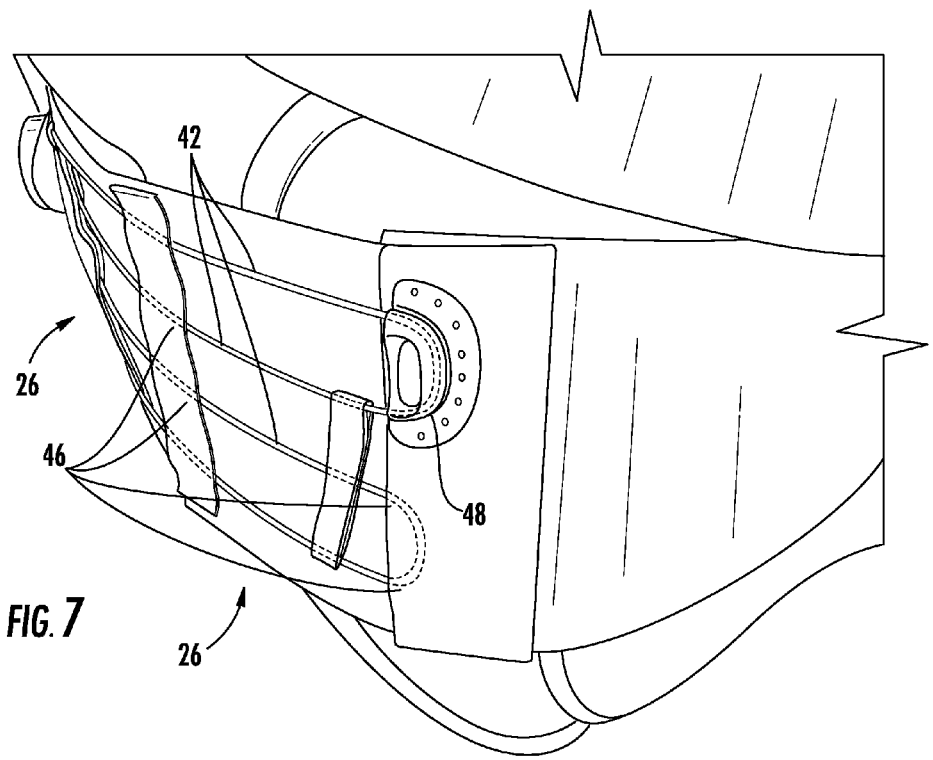
FIG. 7 is a close-up view of a portion of the side member and cable tensioning system of the brace of FIG. 1.
Figure 8:
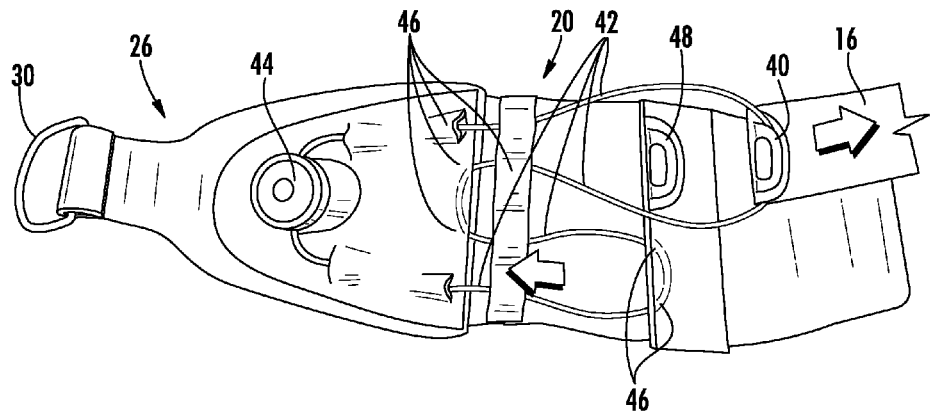
FIG. 8 shows the side member and cable tensioning system of the brace of FIG. 1 cooperating with a shoulder strap for tightening of the shoulder strap.
Figure 9:
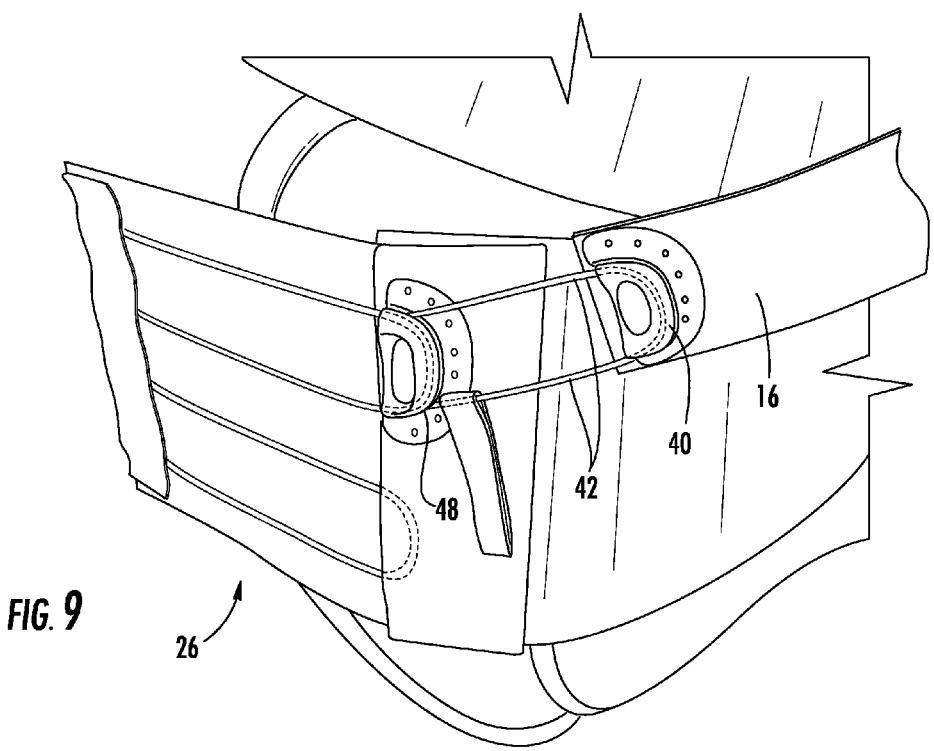
FIG. 9 is a close-up view showing cooperation of the shoulder strap with tensioning system of the brace of FIG. 1.

Desired positioning of the brace 10 is to locate the anterior portion 24 directly above the symphysis pubis of the user, and the posterior portion 22 directly above the sacrococcygeal junction and extending to the scapular spine. The extension 14 is adjusted to provide the desired support, and the tension of the waist portion 12 about the waist of the user may be adjusted by adjusting the cable take-up 44 of one or both of the side members 26 and 28, such as depicted in FIGS. 6 and 7.

At the initial fitting the shoulder straps 16 and 18 may be tensioned by grasping them and pulling down and securing the free ends of the straps 16/18 having the cable guides 40 thereon to the brace 10 as by mating hook and loop material. Thereafter the free ends of each of the straps 16 and 18 being engaged by the cable tensioning systems 20 as by releasing the cable 42 from the releasable cable guide 48 of the side member 26/28 and engaging the cable 42 with the strap cable guide 40 of the strap 16/18. Tension of the waist or abdominal portion 12 may then be adjusted using the tensioning systems 20 while at the same time tightening the shoulder straps 16 and 18 to encourage extension. In this regard, it will be understood that adjustment of the tension may refer to tightening or loosening, as may be indicated to provide a desired fitment of the brace 10 to the user and effect on the user. Thus, the construction off the brace 10, with the adjustment of the straps to enables the brace 10 to be utilized to fit a wide variety of patient indications by adjusting the cable tensions.

For example, the end of the straps 16/18 having the cable guide 40 thereon are secured to the side members 26/28 as by mating hook/loop material. Thus, when the cables 42 are removed from the releasable cable guides 48 on the side members 26/28 and engaged with the strap cable guides 48 on the straps 16/18, adjustment of the cable tensioning systems 20 will adjust the tension of the cables 42 and hence simultaneously adjust both the tension of the waist portion 12 and the straps 16/18.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A spinal brace, comprising:
 a waist portion configured for encircling and being adjustably tensionable about the waist of a user;
 a dorsal lumbar extension extending from a rear portion of the waist portion;
 a shoulder strap positionable to extend over a shoulder of the user and connectable to both the waist portion and the dorsal lumbar extension;
 a cable connected to the waist portion for tensioning only the waist portion about the waist of the user and selectively also connectable to the shoulder strap for simultaneously tensioning both the waist portion and the shoulder strap when the cable is also connected to the shoulder strap; and
 a cable tensioner operably associated with the cable to adjust the tension of the cable, comprising a cable and cable take-up, wherein adjustment of the tension of the cable tensions only the waist portion about the waist of the user when the cable is connected only to the waist portion and simultaneously adjusts the tension of the waist portion of the brace about the waist of the user and the tension of the shoulder strap when the cable is also connected to the shoulder strap.

2. The brace of claim 1, wherein the cable take-up is a cable reel.

3. The brace of claim 1, wherein the cable tensioner includes a cable receiver on the waist portion and a cable receiver on the strap, with the cable being selectively detachable from the receiver on the waist portion and attachable to the receiver on the strap to enable adjustment of the tension of the shoulder strap.

4. The brace of claim 1, wherein the cable take-up is located on the waist portion.

5. A spinal brace, comprising:
 a waist portion configured for encircling and being adjustably tensionable about the waist of a user;
 a shoulder strap positionable to extend over a shoulder of the user and connectable to the waist portion;
 a cable connected to the waist portion for tensioning only the waist portion about the waist of the user and selectively also connectable to the shoulder strap for simultaneously tensioning both the waist portion and the shoulder strap when the cable is also connected to the shoulder strap; and
 a cable tensioner operably associated with the cable to adjust the tension the cable, comprising a cable and a cable take-up, wherein adjustment of the tension of the cable tensions only the waist portion about the waist of the user when the cable is connected only to the waist portion and simultaneously adjusts the tension of the waist portion of the brace about the waist of the user and the tension of the shoulder strap when the cable is also connected to the shoulder strap.

6. The brace of claim 5, wherein the cable tensioner includes a cable reel, a cable receiver on the waist portion, and a cable receiver on the strap, with the cable being selectively detachable from the receiver on the waist portion and attachable to the receiver on the strap to enable adjustment of the tension of the shoulder strap.

7. A spinal brace, comprising:
 a waist portion configured for encircling and being adjustably tensionable about the waist of a user, the waist portion including include a posterior portion, an anterior portion, and first and second side members, each made of a conformable and flexible material, wherein the first and second side members are each releasable and adjustably connectable to the posterior member and the anterior member to enable the formation of the waist portion in a configuration that will snugly encircle the waist of a user;
 a dorsal lumbar extension extending from the posterior portion of the waist portion;
 a first shoulder strap positionable to extend over a first shoulder of the user and connectable to both the first waist portion and the dorsal lumbar extension;
 a second shoulder strap positionable to extend over a second shoulder of the user and connectable to both the second waist portion and the dorsal lumbar extension;
 a first cable connectable to both the first waist portion and the first shoulder strap for tensioning the first waist portion and the first shoulder strap;
 a second cable connectable to both the second waist portion and the second shoulder strap for tensioning the second waist portion and the second shoulder strap;
 a first cable tensioner operably associated with the first cable to adjust the tension the first cable, wherein adjustment of the tension of the first cable simultaneously adjusts the tension of the first waist portion of the brace and the tension of the first shoulder strap; and
 a second cable tensioner operably associated with the second cable to adjust the tension the second cable, wherein adjustment of the tension of the second cable simultaneously adjusts the tension of the second waist portion of the brace and the tension of the second shoulder strap.

8. The brace of claim 7, wherein the first cable tensioner includes a first cable reel located on the first waist portion, a first cable receiver on the first waist portion, and a strap cable receiver on the first strap, with the first cable being selectively detachable from the first receiver on the first waist portion and attachable to the strap receiver on the first strap to enable adjustment of the tension of the first shoulder strap.

* * * * *